United States Patent
Bille et al.

(12)
(10) Patent No.: US 6,382,797 B1
(45) Date of Patent: May 7, 2002

(54) ABERRATION-FREE DELIVERY SYSTEM

(75) Inventors: Josef Bille; Frieder Loesel, both of Heidelberg (DE)

(73) Assignee: 20/10 Perfect Vision Optische Geraete GmbH (DE)

( * ) Notice: Subject to any disclaimer, the term of this patent is extended or adjusted under 35 U.S.C. 154(b) by 29 days.

(21) Appl. No.: 09/690,776

(22) Filed: Oct. 17, 2000

(51) Int. Cl.[7] ................................................. A61B 3/10
(52) U.S. Cl. ....................................................... 351/212
(58) Field of Search ................................. 351/205, 206, 351/211, 212, 214, 220, 221; 356/124, 125, 128; 606/4, 5

(56) References Cited

U.S. PATENT DOCUMENTS

| | | |
|---|---|---|
| 4,579,430 A | 4/1986 | Bille |
| 5,949,521 A | 9/1999 | Williams |
| 6,220,707 B1 * | 4/2001 | Bille ........................... 351/212 |
| 6,234,631 B1 * | 5/2001 | Sarver et al. ................ 351/212 |
| 6,271,915 B1 * | 8/2001 | Frey et al. ................... 356/124 |
| 6,331,059 B1 * | 12/2001 | Kudryashov et al. ........ 351/221 |

* cited by examiner

*Primary Examiner*—George Manuel
(74) *Attorney, Agent, or Firm*—Nydegger & Associates

(57) ABSTRACT

A device and method for establishing an aberration-free delivery system for use in evaluating an optical specimen includes a light source for directing light through the system and along a beam path toward the specimen. A first beam splitter is positioned on the beam path to direct light radiated from the system toward a detector for creation of a first wavefront, and for generation of a signal. In turn, the signal is used to program an active mirror that is also positioned on the beam path, to thereafter establish an aberration-free wavefront for light incident on the optical specimen. Further, a second beam splitter is positioned on the beam path for directing light reflected from the specimen toward the detector for the creation of a second wavefront having characteristics of optical aberrations in the specimen. The second wavefront is then used to further program the active mirror for analysis and evaluation of the optical specimen.

20 Claims, 1 Drawing Sheet

ABERRATION-FREE DELIVERY SYSTEM

FIELD OF THE INVENTION

The present invention pertains generally to surgical and diagnostic systems that use light as the operative medium. More particularly, the present invention pertains to light beam delivery systems, and methods for their use, which generate aberration-free light beams that are useful for ophthalmologic purposes. The present invention is particularly, but not exclusively, useful for incorporating an active mirror into a light delivery system for the purpose of generating an aberration-free light beam.

BACKGROUND OF THE INVENTION

Whenever an object is to be measured, evaluated or somehow modified, it is absolutely necessary that some base reference be established from which the precision and accuracy of the accomplished task can be determined. In order to do this, for some applications it is necessary that the system, device or apparatus being used, be able to accurately and reliably establish its own base reference.

In the field of ophthalmology, the systems that are used for generating surgical light beams, or for making optical measurements, are, in general, extremely sensitive and extraordinarily susceptible to environmental changes. For instance, in addition to the more obvious perturbations and disturbances that may be caused by physically jostling optical equipment, the temperature and humidity conditions in the operational environment may also cause these optical systems to fall out of alignment (i.e. move away from the base reference). Consequently, in order to maintain their accuracy and reliability during an operation, optical systems should be capable of adapting to dynamic changes, as well as being statically stable. Further, in addition to the environmental factors that can affect the operation of an optical system, the physical components of an optical system (e.g. lenses, mirrors, filters and beam splitters) can also affect the operation. This will be so for all applications, under any condition. Still further, there are applications wherein the aberrations that are contributed by the optical specimen may also be important and need to be accounted for (e.g. retinal surgery). In any event, the specific instance wherein wavefront analysis techniques are to be employed, the ability of an optical system to accurately establish and precisely maintain its base reference is critical.

Wavefront analysis techniques rely on the notion that the individual component rays of a light beam will speed up or slow down at different rates according to their refractive history. For wavefront analysis, a plane wavefront, i.e. one wherein all of the individual component rays of light arrive at a same distance from their common source at the same time, serves as a useful and identifiable base reference. Thus, if a light beam is known or is established to have a plane wavefront, any perturbations or disturbances to the light beam will introduce aberrations which cause the wavefront of the light beam to become somehow distorted. Recently, it has been possible to effectively measure such distortions using devices such as a Hartmann-Shack sensor.

As indicated above, for specific applications wherein the purpose of a light beam delivery system needs to account for the optical characteristics of a specimen, such as an eye, it is desirable to isolate the optical aberrations that are introduced by the specimen. As mentioned above, these aberrations will manifest themselves as changes in the wavefront of the light beam that has passed through the specimen. Accordingly, if changes in the wavefront that result when light passes through the specimen can be determined, the optical characteristics of the specimen can also be determined. This, of course, requires the changes in the wavefront be measured. A convenient base reference for these purposes is a plane wavefront, or some other definable and ascertainable wavefront.

In light of the above, it is an object of the present invention to provide a light delivery system for use in evaluating an optical specimen, that effectively generates an aberration-free wavefront for the light beam as it is incident on the specimen, or after it has passed through the specimen. Another object of the present invention is to provide a light beam delivery system that employs a programmable active mirror, for generating an aberration-free light beam that can be subsequently used for surgical or diagnostic purposes. Still another object of the present invention is to provide a light beam delivery system that maintains an essentially aberration-free light beam despite dynamic changes in the environmental factors that would otherwise affect the optical alignment of the system. Another object of the present invention is to provide a light beam delivery system that will optically isolate a specimen so that it can be evaluated free of interfering distortions from other sources. Yet another object of the present invention is to provide a light beam delivery system that is relatively easy to manufacture, is simple to use, and is comparatively cost effective.

SUMMARY OF THE PREFERRED EMBODIMENTS

In accordance with the present invention, a device and method for establishing an aberration-free delivery system for use in evaluating, altering or modifying an optical specimen envisions accounting for optical aberration in a two step process. The first step involves compensating for those optical aberrations that are introduced by the delivery system. The second step, if necessary or desired, involves compensating for the optical aberrations that are introduced by the optical specimen itself.

In detail, the delivery system of the present invention includes a light source. Specifically, the light source directs a light beam through the delivery system and toward the specimen. More specifically, after passing through the delivery system, the light beam is directed along a beam path toward an active mirror and it is then reflected from the active mirror toward the specimen. Included are a first beam splitter and a second beam splitter that are sequentially positioned on the beam path between the active mirror and the specimen. The purpose of the first beam splitter is to direct about ten percent of the light that is reflected from the active mirror toward a detector before this light is incident on the specimen. Importantly, however, this happens after the light has passed through the delivery system. On the other hand, the purpose of the second beam splitter is to direct light that is subsequently reflected from the optical specimen toward the detector. For the present invention, the detector is preferably a device such as a Hartmann-Shack sensor.

In the first operational step for the present invention, the light that is reflected toward the detector by the first beam splitter will be characterized by a first wavefront. The important consideration here is that this first wavefront includes all of the aberrations that were introduced into the light beam as it passed through the delivery system. A computer/comparator then compares this first wavefront with a base reference (e.g. a plane wavefront), and generates a signal(s) which is indicative of the difference between the first wavefront and the base reference. This signal is then used to program the active mirror so that, in the first operation step, the light reflected toward the specimen from the active mirror will be an essentially aberration-free light beam.

For applications wherein the objective is to generate only a plane wavefront, the second step of the present invention can be omitted. However, if the optical aberrations that are contributed by the specimen are also required, such as for retinal surgery, the present invention envisions an evaluation of the optical specimen in the second step.

In the second step, as a result of implementing the first step, a plane wavefront is reflected from the active mirror and is directed toward the specimen. As this light is reflected from the specimen it will have a second wavefront which is indicative of only the optical aberrations that are contributed by the specimen. The second beam splitter then directs this second wavefront toward the detector. Next, the computer/comparator compares the second wavefront with a base reference (e.g. a plane wavefront), and generates a signal(s) which is indicative of the difference between the second wavefront and the base reference. This signal can then be used to program the active mirror so that light reflected from the active mirror toward the specimen will be a negative of the aberration contribution from the optical specimen. This negative will then cancel the aberration contribution of the optical specimen and the result will be an essentially aberration-free light beam.

In accordance with the present invention, by implementing only the first step, the system can use closed-loop control of the active mirror to maintain the first wavefront as an aberration-free, plane wavefront. Thus, corrections to this first wavefront can be continuously pre-programmed into the active mirror (i.e. continuous closed-loop control). Alternatively, when both steps are implemented, closed-loop control of the active mirror can be accomplished to establish the second wavefront as desired. In this case, the first step can be periodically made at predetermined time intervals (i.e. a hybrid open/closed-loop control) to account for changes in the optical aberration contribution of the delivery system.

As will be appreciated by the skilled artisan, the second wavefront can be analyzed by the computer/comparator to evaluate the optical specimen for surgical or diagnostic purposes. Further, as envisioned by the present invention, the light that is used for programming the active mirror, and the light that is used to surgically alter or modify the optical specimen, can have different wavelengths.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

The FIGURE is a schematic drawing of the present invention showing the interrelationship of its component elements.

DESCRIPTION OF THE PREFERRED EMBODIMENT

Figure 1:
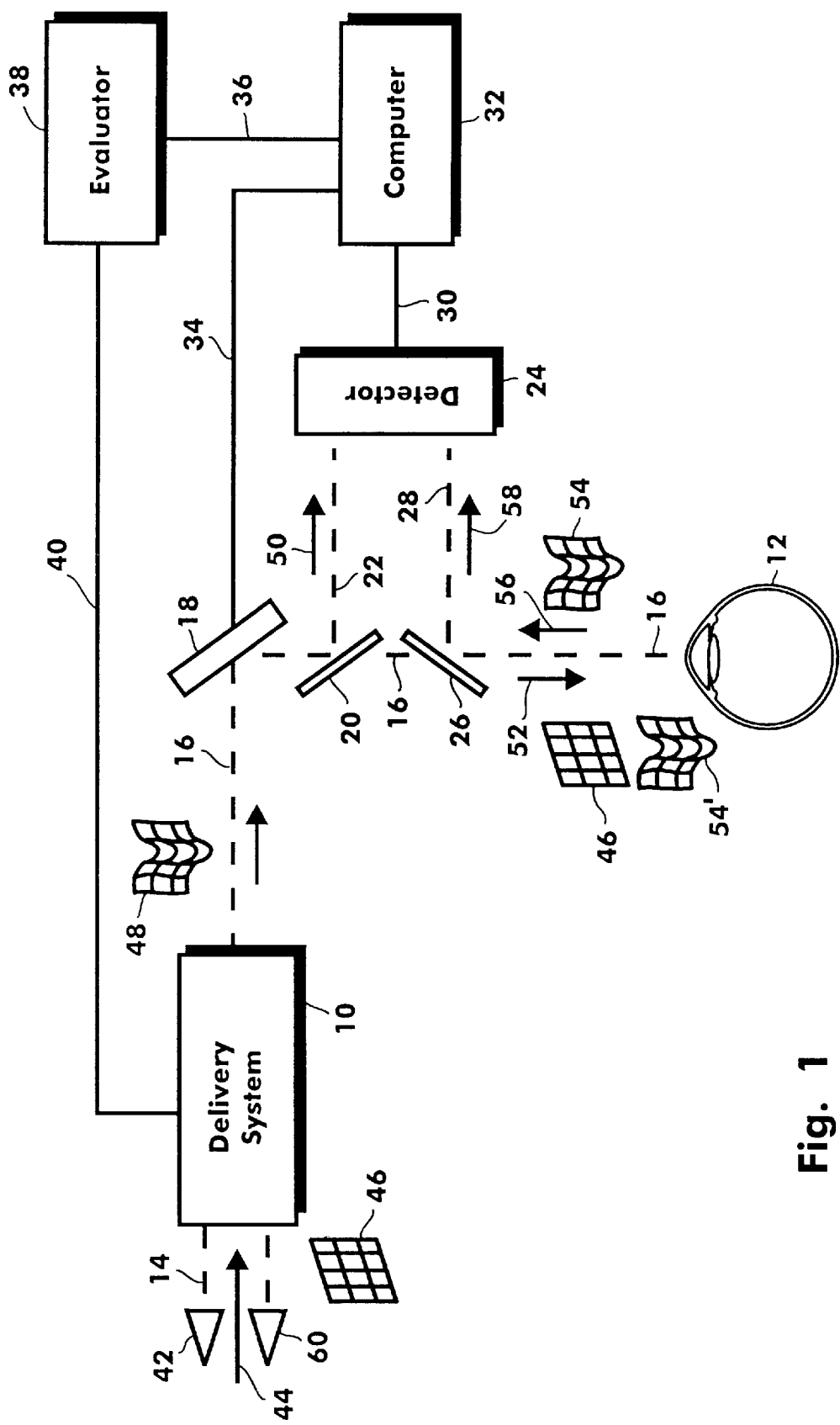

Referring to the FIGURE, it is to be appreciated that the present invention pertains to a delivery system 10, and the interaction between the delivery system 10 and a specimen 12. More specifically, the delivery system 10 will include an arrangement of optical components that form and direct a light beam 14 into incidence on the specimen 12. For purposes of the present invention, although other essentially transparent objects can be evaluated, the specimen 12 will most likely be a human eye. As further envisioned by the present invention, the delivery system 10 is able to maneuver the light beam 14 onto the beam path 16 toward the specimen 12 for either surgical or diagnostic purposes. For these purposes, the delivery system 10 of the present invention can include any of the many various optical components that are presently known in the pertinent art.

Included in the present invention is an active mirror 18 which is located on the beam path 16 between the delivery system 10 and a beam splitter 20. Preferably, the active mirror 18 is of a type that is disclosed and claimed by Bille in U.S. application Ser. No. 09/512,440 for an invention entitled "Method for Programming an Active Mirror to Mimic a Wavefront," which is assigned to the same assignee as the present invention. Further, the beam splitter 20 is preferably of a type that transmits approximately ninety percent (90%) of the light traveling on the beam path 16 toward the specimen 12. The ten percent (10%) of the light in light beam 14 that is diverted by the beam splitter 20 will then be directed along the beam path 22 to a detector 24. As intended for the present invention, the detector 24 will be a device known in the pertinent art that is capable of analyzing wavefronts, such as a Hartmann-Shack sensor.

The ninety percent (90%) of the light beam 14 that is transmitted by the beam splitter 20 will continue along the beam path 16 and pass through another beam splitter 26 en route to its incidence on the specimen 12. Light reflected from the specimen 12, back along the beam path 16, will then be diverted by the beam splitter 26 along a beam path 28 toward the detector 24. It is also shown in the FIGURE that the detector 24 is connected via a line 30 with a computer/comparator 32, and that the computer/comparator 32 is connected via a line 34 with the active mirror 18. Additionally, the FIGURE shows that the computer/comparator 32 is connected via a line 36 with an evaluator 38, and that the evaluator 38 is connected via a line 40 with the delivery system 10.

In operation, a light source 42 directs a light beam 14 toward the delivery system 10 in the direction of the arrow 44 with a plane wavefront 46. While passing through the delivery system 10, however, the light in light beam 14 is distorted by optical components (not shown) inside the delivery system 10. The consequence of this is that when the light is radiated from the system 10, and onto the beam path 16, it will have a distorted (first) wavefront 48. This distorted (first) wavefront 48 is then reflected from the active mirror 18. Initially, for purposes of establishing proper optical corrections for the delivery system 10, the active mirror 18 will be programmed as a flat surface. Thus, during the set up phase, the active mirror 18 does not introduce any additional distortions into the wavefront 48. Then, after being reflected from the active mirror 18, the distorted (first) wavefront 48 is directed by the beam splitter 20 in the direction of arrow 50, along the beam path 22, to the detector 24.

The detector 24 is used by the present invention to identify and define the distorted (first) wavefront 48. The detector 24 then sends information about the distorted (first) wavefront 48 to the computer/comparator 32 for analysis. In turn, the computer/comparator 32 will compare this information with a base reference (e.g. a plane wavefront 46) and generate a signal(s) that is(are) indicative of the differences between the distorted (first) wavefront 48 and the base reference. The signal(s) is(are) then sent via the line 34 to the active mirror 18 for the purposes of programming the active mirror 18. Once so programmed, it is intended that the active mirror 18 can be further programmed to alter the distorted (first) wavefront 48 that is being radiated from the delivery system 10. Specifically, it is intended that the active mirror 18 will compensate for the distorted (first) wavefront 48 so that light reflected from the active mirror 18 will have a plane wavefront 46 as it travels from the active mirror 18 along the beam path 16, and in the direction of arrow 52 toward the specimen 12. The generation of plane wavefront 46 is indicative of the first step in the operation of the present invention.

Importantly, as light enters the specimen 12, from the delivery system 10 during the first operational step of the present invention, the light will have a plane wavefront 46. However, due to optical aberrations that are introduced by the specimen 12, the light that is reflected from specimen 12 back along the path 16 in the direction of arrow 56 will exhibit a distorted (second) wavefront 54. This distorted (second) wavefront 54 will then be directed by the beam splitter 26 along the beam path 28 in the direction of arrow 58 toward the detector 24. In a manner similar to that discussed above with regard to the distorted (first) wavefront 48, the detector 24 will identify and define the distorted (second) wavefront 54. Information about the distorted (second) wavefront 54 will then be sent to the computer/comparator 32, and further sent via line 36 to the evaluator 38. Depending upon the purposes of the delivery system 10, if desired, the evaluator 38 can use information about the distorted (second) wavefront 54 to control the delivery system 10.

In the second operational step for the present invention, the distorted (second) wavefront 54 can also be used to program the active mirror 18. Specifically, in addition to whatever programming of the active mirror 18 that was accomplished during the first step, the active mirror 18 can be further programmed with a negative of the second wavefront 54 (i.e. a wavefront 54'). The consequence here is that whatever optical aberrations are introduced by the specimen 12 to create wavefront 54 will be canceled by the negative wavefront 54' of the light that will be incident on the specimen 12.

In summary, for the first operational step envisioned by the present invention, the active mirror 18 begins as a flat surface. Due to optical aberrations in the system 10, a distorted (first) wavefront 48 is reflected from the flat active mirror 18. The distorted (first) wavefront 48 is then used to program and reconfigure the active mirror 18 to eliminate the optical aberrations that are contributed by the delivery system 10. A plane wavefront 46 is then reflected by the active mirror 18 toward the specimen 12. As stated above, this plane wavefront 46 is indicative of the first step. In the second step, the active mirror 18 is further programmed to eliminate the optical aberrations that are contributed by the specimen 12. This is possible because after the plane wavefront 46 is incident on the specimen 12 it is reflected as the distorted (second) wavefront 54. The computer/comparator 32 can then further program the active mirror 18 so that a negative wavefront 54' is reflected from the active mirror 18. This negative wavefront 54' will then cancel the optical aberration contributions of the specimen 12.

As envisioned for the present invention, one light source 42 can be used for purposes of programming the active mirror 18 in both the first and second operation steps. Another light source 60 can then be used on the specimen 12 for surgical or diagnostic purposes. It will be appreciated that the wavelengths of light generated by the respective light sources 42 and 60 can be different, and that the light sources 42 and 60 can be operated either simultaneously or independently. In all instances, however, it is an important aspect of the present invention that the distorted (first) wavefront 48 is compensated by the active mirror 18 so that a plane wavefront 46 is incident on the specimen 12 in the first step. Consequently, the specimen 12 is optically isolated from the delivery system 10, and the light reflected from the specimen 12 will have a distorted (second) wavefront 54 that includes only aberrations that are introduced by the specimen 12. This second wavefront 54 can then be used as desired. In one application it is envisioned that with the creation of the negative wavefront 54' incident on an eye, optical aberrations that would otherwise be introduced by the cornea can be canceled. The result is that the light can pass through the cornea and be incident on the retina with a plane wavefront (e.g. plane wavefront 46).

While the particular Aberration-free Delivery System as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for establishing an aberration-free delivery system for use in evaluating an optical specimen, wherein the system directs light along a beam path toward the specimen, said device comprising:

a detector;

an active mirror positioned on said beam path between said system and said specimen;

a first beam splitter positioned on said beam path between said active mirror and said specimen for directing a portion of the light radiated from said system toward said detector for creation of a first wavefront, said first wavefront having characteristics of optical aberrations in said system;

a means for generating a signal indicative of said first wavefront, said signal generating means being connected to said active mirror for selectively programming said active mirror with said signal to establish an aberration-free wavefront for light from said system incident on the optical specimen;

a second beam splitter positioned on said beam path between said first beam splitter and said specimen for directing a portion of the light reflected from said specimen toward said detector for creation of a second wavefront, said second wavefront having characteristics of optical aberrations in said specimen; and a means for analyzing said second wavefront to evaluate the optical specimen.

2. A device as recited in claim 1 further comprising a means for generating a signal indicative of a negative said second wavefront, said signal generating means being connected to said active mirror for selectively programming said active mirror with said signal to establish a negative said second wavefront for light from said system incident on the optical specimen to cancel optical aberrations contributed by the specimen.

3. A device as recited in claim 1 wherein said signal generating means includes a means for comparing said first wavefront with a plane wavefront to generate said signal.

4. A device as recited in claim 1 wherein said first beam splitter transmits approximately ninety percent (90%) of the light from said system toward the optical specimen.

5. A device as recited in claim 1 further comprising a first light source for directing light through said system to create said first wavefront and for directing light through said system for reflection from the optical specimen to create said second wavefront, and wherein light from said first light source has a wavelength of approximately six hundred and fifty nanometers (650 nm).

6. A device as recited in claim 5 further comprising a second light source for altering the optical specimen wherein light from said second light source has a wavelength of approximately seven hundred and fifty nanometers (750 nm).

7. A device as recited in claim 1 wherein said active mirror is pre-programmed with said signal.

8. A device as recited in claim 1 wherein said detector is a Hartmann-Shack sensor.

9. A device as recited in claim 1 wherein said optical aberrations in said system include dynamic aberrations and static aberrations.

10. A device as recited in claim 1 wherein said optical aberrations in the optical specimen include dynamic aberrations and static aberrations.

11. A method for establishing an aberration-free delivery system for use in evaluating an optical specimen, wherein the system directs light along a beam path toward the specimen, said method comprising the steps of:

positioning an active mirror on said beam path between said system and said specimen;

directing a portion of the light radiated from said system toward said detector for creation of a first wavefront, said first wavefront having characteristics of optical aberrations in said system;

selectively generating signals indicative of said first wavefront, said signals being used to program said active mirror to establish an aberration-free wavefront;

directing a portion of the light reflected from said specimen toward said detector for creation of a second wavefront, said second wavefront having characteristics of optical aberrations in said specimen; and analyzing said second wavefront to evaluate the optical specimen.

12. A method as recited in claim 11 further comprising the step of selectively generating signals indicative of said second wavefront, said signals being used to program said active mirror to establish a negative said second wavefront for light from said system incident on the optical specimen to cancel optical aberrations contributed by the specimen.

13. A method as recited in claim 12 wherein said analyzing step is accomplished using a Hartmann-Shack sensor.

14. A method as recited in claim 12 further comprising the step of comparing said first wavefront with a plane wavefront to generate said signals.

15. A method as recited in claim 14 wherein said comparing step is accomplished using a Hartmann-Shack sensor.

16. A method as recited in claim 12 wherein said directing step further comprises the steps of:

using a first light source for directing light through said system to create said first wavefront and said second wavefront; and using a second light source for altering the optical specimen.

17. A method as recited in claim 16 wherein light from said first light source has a wavelength of approximately six hundred and fifty nanometers (650 nm) and light from said second light source has a wavelength of approximately seven hundred and fifty nanometers (750 nm).

18. A method as recited in claim 12 further comprising the step of pre-programming said active mirror with said signals.

19. A method as recited in claim 12 wherein said optical aberrations in said system include dynamic aberrations and static aberrations.

20. A method as recited in claim 12 wherein said optical aberrations in the optical specimen include dynamic aberrations and static aberrations.

* * * * *